(12) United States Patent
Xu et al.

(10) Patent No.: US 7,339,054 B2
(45) Date of Patent: Mar. 4, 2008

(54) PROCESS FOR PREPARING BRANCHED RIBONUCLEOSIDES FROM 1,2-ANHYDRORIBOFURANOSE INTERMEDIATES

(75) Inventors: Feng Xu, Staten Island, NY (US); Matthew M Bio, London (GB); Cameron Cowden, Hoddesdon (GB); Kimberly A. Petrillo, Philadelphia, PA (US); J. Michael Williams, Hillsborough, NJ (US); Chunhua Yang, Edison, NJ (US); Marjorie See Waters, Cranbury, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/544,575

(22) PCT Filed: Feb. 6, 2004

(86) PCT No.: PCT/US2004/003469

§ 371 (c)(1),
(2), (4) Date: May 19, 2006

(87) PCT Pub. No.: WO2004/072090

PCT Pub. Date: Aug. 26, 2004

(65) Prior Publication Data

US 2007/0037771 A1 Feb. 15, 2007

Related U.S. Application Data

(60) Provisional application No. 60/446,935, filed on Feb. 12, 2003.

(51) Int. Cl.
*C07H 19/14* (2006.01)
*C07D 487/00* (2006.01)

(52) U.S. Cl. .................... 536/27.11; 536/27.2; 544/262

(58) Field of Classification Search .................... None
See application file for complete search history.

(56) References Cited

U.S. PATENT DOCUMENTS

| 3,037,980 | A | 6/1962 | Hichings et al. |
| 3,480,613 | A | 11/1969 | Walton |
| 6,777,395 | B2 | 8/2004 | Bhat et al. |

FOREIGN PATENT DOCUMENTS

| WO | WO 01/90121 | 11/2001 |
| WO | WO 01/92282 | 12/2001 |
| WO | WO 02/32920 | 4/2002 |
| WO | WO 02/057287 | 7/2002 |
| WO | WO 02/057425 | 7/2002 |
| WO | WO2004/072090 A1 * | 8/2004 |
| WO | WO2006/065335 A2 * | 6/2006 |

OTHER PUBLICATIONS (R) Bio et al., "Practical Synthesis of a Potent Hepatitis C Virus RNA Replication Inhibitor," J. Organic Chemistry, 69(19), 6257-6266 (2004); web published Aug. 13, 2004.*

Beigelman et al., "New Syntheses of 2'-C-Methylnucleosides Starting from D-Glucose and D-Ribose", Carbohydrate Research, vol. 166, pp. 219-232 (1987).

Matsuda, et al., "Alkyl Addition Reaction of Pyrimidine 2'-Ketonucleosides: Synthesis of 2'-Branched-Chain Sugar Pyrimidine Nucleosides (Nucleosides and Nucleotides LXXXI)", Chemical Pharmaceutical Bulletin, vol. 36, Iss. 3, pp. 945-953 (1988).

Wolfe, et al., "A Concise Synthesis of 2'-C-Methylribonucleosides", Tetrahedron Letters, vol. 36, No. 42, pp. 7611-7614 (1995).

Harry-O'kuru, et al., "A Short, Flexible Route towards 2'-C-Branched Ribonucleosides", J. Org. Chem., vol. 62, pp. 1754-1759 (1997).

Murai et al, "A Synthesis and an X-Ray Analysis of 2'-C-, 3'-C- and 5'-C- Methylsangivamycins", Heterocycles, vol. 33, No. 1, pp. 391-404 (1992).

Wolf, et al., "New 2'-C-Branched-Chain-Sugar Nucleoside Analogs with Potential Antiviral or Antitumor Activity", Synthesis, pp. 773-778 (1992).

Gallo, et al., "Synthesis of 2'-Modified Nucleotides", Molecules, vol. 5, pp. 727-729 (2000).

Ning, et al.,"Synthesis and glycosidic coupling reaction of substituted 2,6-dioxabicylo[3.1.0]hexanes: 1,2-anhydro-3,5-di-O-benzyl-α-D-ribofuranose", Carbohydrate Research, vol. 300, pp. 355-360 (1997).

Ning, et al., "A facile synthesis of 1-5'-O-acetyl-3'-O-benzyl-β-D-xylofuranosyl)thymidine: a potentially viable intermediate for the prepaation of the anti-AIDS drugs, AZT and D4T", Carbohydrate Research, vol. 326, pp. 235-239 (2000).

* cited by examiner

*Primary Examiner*—L. E. Crane
(74) *Attorney, Agent, or Firm*—Kenneth R. Walton; Seldon O. Heber; Philippe L. Durette

(57) ABSTRACT

A process is provided for the preparation of branched-chain ribonucleosides of formula (I):

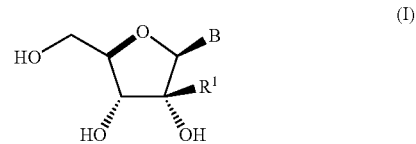

from the 1,2-anhydroderivatives of formula (II).

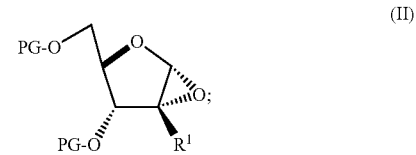

wherein PG is a hydroxyl protecting group, B is a purine or pyrimidine nucleobase, and $R^1$ is $C_{1-6}$ alkyl. The compounds of formula (I) are inhibitors of HCV polymerase useful in the treatment of HCV infection.

13 Claims, No Drawings

PROCESS FOR PREPARING BRANCHED RIBONUCLEOSIDES FROM 1,2-ANHYDRORIBOFURANOSE INTERMEDIATES

CROSS REFERENCE TO RELATED APPLICATIONS

This application is the National Stage of International Application No. PCT/US04/003469, filed 6 Feb. 2004, which claims the benefit under 35 U.S.C. 119(e) of U.S. Provisional Application No. 60/446,935 filed 12 Feb. 2003.

FIELD OF THE INVENTION

The present invention is concerned with a novel process for the preparation of 2'-C-branched ribonucleosides which are inhibitors of hepatitis C viral (HCV) polymerase useful for the treatment of HCV infection.

BACKGROUND OF THE INVENTION

2'-C-Alkylribonucleosides have been described in the patent literature as inhibitors of HCV RNA-dependent RNA polymerase and thereby useful for the treatment of HCV infection. Reference is made to the following publications of international patent applications which disclose branched-chain ribonucleoside inhibitors of HCV polymerase: WO 01/90121 (29 Nov. 2001) and WO 01/92282 (6 Dec. 2001) both assigned to Novirio Pharmaceuticals and Universita degli Studi di Cagliari; WO 02/32920 (25 Apr. 2002) assigned to Pharmasset Limited; and WO 02/057287 (25 Jul. 2002) and WO 02/057425 (25 Jul. 2002) assigned jointly to Merck & Co. and Isis Pharmaceuticals. Synthetic approaches to 2'-C-branched ribonucleosides have previously been described in the chemical and patent literature: FR 1521076 (12 Apr. 1968); U.S. Pat. No. 3,480,613 (25 Nov. 1969); GB Patent No. 1209654 (21 Oct. 1970); S. R. Jenkins et al. *Carbohydrate Res.*, 166: 219-232 (1987); A. Matsuda et al., *Chem. Pharm. Bull.*, 36: 945-953 (1988); M. S. Wolfe et al., "A Concise Synthesis of 2'-C-Methylribonucleosides," *Tetrahedron Lett.*, 42: 7611-7614 (1995); R. E. Harry-O'kuru et al., "A Short, Flexible Route toward 2'-C-branched Ribonucleosides," *J. Org. Chem.*, 62: 1754-1759 (1997); Y. Murai et al., "A Synthesis and X-Ray Analysis of 2'-C-, 3'-C-, and 5'-C-Methylsangivamycins," *Heterocycles*, 33: 391-404 (1992); J. Wolf et al., *Synthesis*, 773-778 (1992); and M. Gallo et al., "Synthesis of 2'-Modified Nucleotides," *Molecules*, 5: 727-729 (2000). Although the synthetic methods disclosed in these references suffice to prepare small quantities of the desired branched-chain ribonucleosides, they suffer from low and variable yields in the key glycosylation step to elaborate the nucleosidic bond in a stereoselective fashion and therefore are not amenable from an economic perspective to scale-up for the production of kilogram quantities required for preclinical and clinical use.

The present invention provides a novel process for the preparation of 2'-C-alkylribonucleosides which are inhibitors of HCV polymerase useful for the treatment of HCV infection.

SUMMARY OF THE INVENTION

This invention is concerned with a process for preparing 2'-C-alkylribonucleosides of structural formula I:

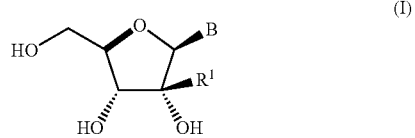

wherein $R^1$ is $C_{1-6}$ alkyl and B is a purine or pyrimidine nucleobase selected from the group consisting of cytosine, uracil, thymine, hypoxanthine, adenine, guanine, 7-deazaguanine, 7-deazaadenine, 7-deaza-2,6-diaminopurine, and 7-deazahypoxanthine.

DETAILED DESCRIPTION OF THE INVENTION

The process of the present invention involves the preparation of a compound of structural formula I:

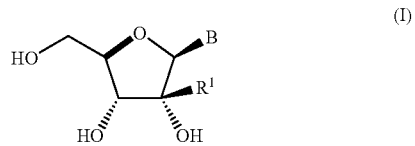

wherein $R^1$ is $C_{1-6}$ alkyl and B is a purine or pyrimidine nucleobase selected from the group consisting of cytosine, uracil, thymine, hypoxanthine, adenine, guanine, 7-deazaguanine, 7-deazaadenine, 7-deaza-2,6-diaminopurine, and 7-deazahypoxanthine;

comprising the steps of:

(a) producing a compound of structural formula II:

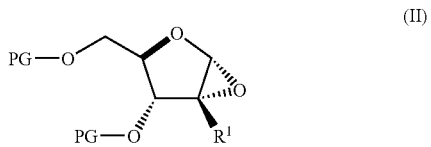

wherein PG is a hydroxyl protecting group, by treating a compound of structural formula III:

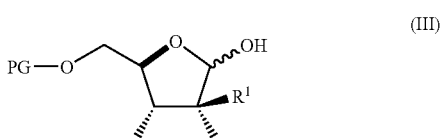

with a sulfonylating or halogenating agent in a suitable organic solvent in the presence of base, wherein said base is added before, during, or after said treatment with said sulfonylating or halogenating agent;

(b) producing a compound of structural formula IV:

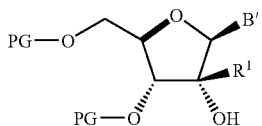

(IV)

wherein B' is optionally protected B, by contacting a compound of structural formula II:

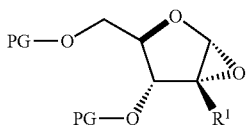

(II)

with a nucleophile B' in a suitable organic solvent; and (c) removing the hydroxyl protecting groups PG and optional protecting groups in B' to afford a compound of structural formula I.

In one embodiment of the process of the present invention, B is guanine, cytosine, adenine, or 7-deazaadenine. In a class of this embodiment, B is 7-deazaadenine. In another embodiment of the process of the present invention, $R^1$ is methyl. In a class of this embodiment, B is 7-deazaadenine.

Structural representations of the various nucleobases of the present invention are provided below:

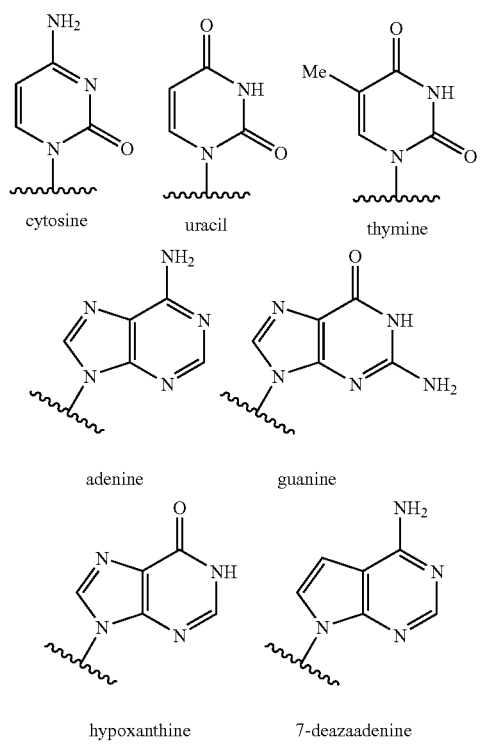

cytosine  uracil  thymine adenine  guanine hypoxanthine  7-deazaadenine

-continued

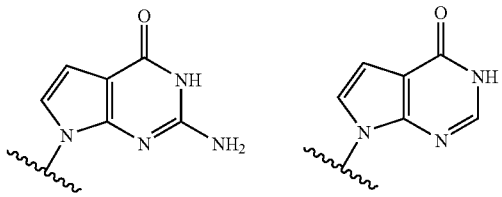

7-deazaguanine  7-deazahypoxanthine

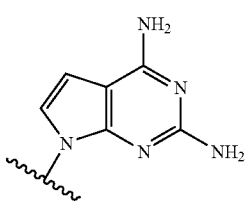

7-deaza-2,6-diamino-purine

The starting point for the process of the present invention is a compound of structural formula III:

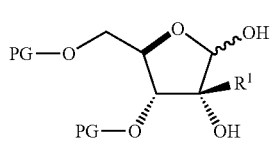

(III)

wherein PG is a hydroxyl protecting group. PG may be an ester, a silyl ether or a benzyl ether protecting group. The benzyl ether protecting group may be substituted with one to two groups independently selected from halogen, cyano, methyl, nitro, and methoxy. Intermediate III wherein PG is an optionally substituted benzyl ether may be prepared according to methods described in PCT International Applications WO 02/057425 (25 Jul. 2002) and WO 02/057287 (25 Jul. 2002).

One embodiment of an ester protecting group is a benzoate ester unsubstituted or substituted with one to two groups independently selected from halogen, cyano, methoxy, nitro, and methyl. In a class of this embodiment the substituted benzoate ester is a p-methylbenzoate ester (p-toluoate ester). Silyl ethers which are useful to protect the sugar hydroxyls include, but are not limited to, trimethylsilyl ether (TMS ether), triethylsilyl ether (TES ether), triisopropylsilyl ether (TIPS ether), t-butyldimethylsilyl ether (TBDMS ether), and t-butyldiphenylsilyl ether (TBDPS ether). Benzyl ethers which are useful to protect the sugar hydroxyls include benzyl, 4-chlorobenzyl, 4-methoxybenzyl, and 2,4-dichlorobenzyl.

Compounds of structural formula III wherein PG is an ester protecting group, such as an optionally protected benzoate, may be prepared according to the procedures depicted in Scheme 1.

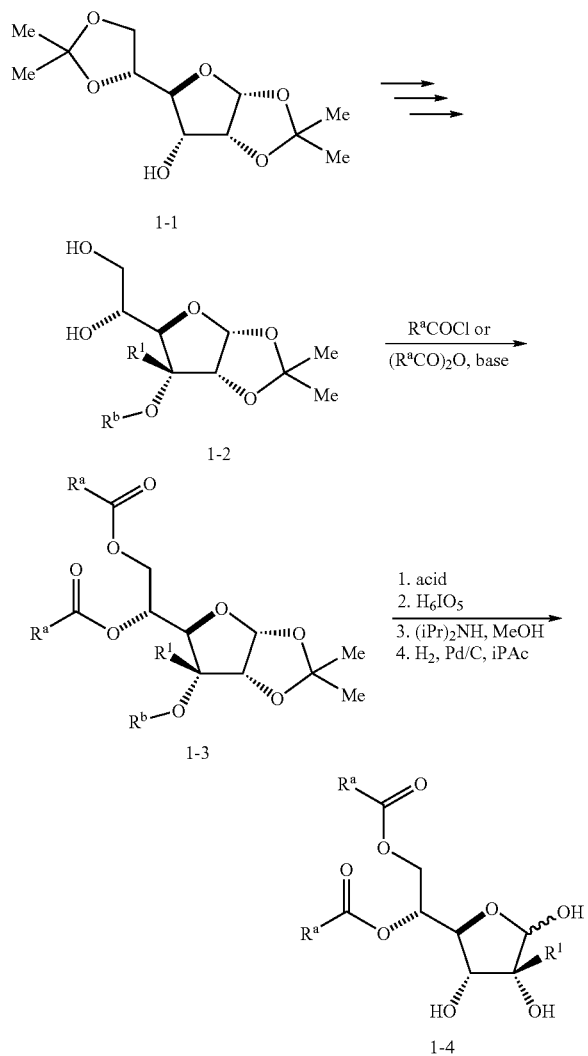

Scheme 1

An efficient preparation of Intermediate 1-2 wherein $R^1$ is methyl and $R^b$ is benzyl is described by M. Funabashi, et al., in *Carbohydrate Research*, Volume 44, page 275-283, 1975.

The first step in the process of the present invention is the construction of the 1,2-anhydroribofuranose intermediate of structural formula II. The 1,2-anhydride (epoxide) functions as a glycosylating agent to provide the desired branched ribonucleoside in a stereoselective fashion. The diol to epoxide transformation is accomplished by treatment of a 1,2-diol of formula III with a sulfonylating agent or halogenating agent either in the presence of a base, such as an amine, amidine, or guanidine base, in a suitable organic solvent, or initially with a sulfonylating or halogenating agent in a suitable organic solvent and subsequently with a suitable base, such as a hindered alkali metal alkoxide, such as potassium t-butoxide. The formation of the epoxide from the diol is carried out at a temperature of about −10 to about 50° C. Sulfonylating agents which are efficient in effecting the formation of the 1,2-anhydride include, but are not limited to, methanesulfonyl chloride, trifluoromethanesulfonyl chloride, benzenesulfonyl chloride, p-toluenesulfonyl chloride, and the corresponding sulfonic anhydrides. Halogenating agents include thionyl chloride, oxalyl chloride, and hydrogen halide (HBr or HCl) in acetic acid. Embodiments of amine bases include triethylamine, pyridine, 4-(dimethylamino)pyridine (DMAP), N,N-diisopropylethylamine, and diisopropylamine; embodiments of amidine or guanidine bases include 1,5-diazabicyclo[4.3.0]non-5-ene and 1,1,3,3-tetramethylguanidine. The diol to epoxide conversion is carried out in a suitable organic solvent such as methylene chloride, chloroform, 1,2-dichloroethane, ethyl acetate, isopropyl acetate (iPAc), tetrahydrofuran, benzene, toluene, diethyl ether, acetonitrile, N,N-dimethylformamide (DMF), N,N-dimethylacetamide (DMAC), and 1,3-dimethyl,3,4,5,6-tetrahydro-2(1H)-pyrimidinone (DMPU), and mixtures thereof. Alternatively, the base is added after reaction with the sulfonylating or halogenating agent. The resulting epoxide is then treated at a temperature of about 15 to about 100° C. with the appropriately protected nucleobase nucleophile to afford the desired protected 2'-C branched ribonucleoside.

When B represents 7-deazaadenine, 7-deazaguanine, or 7-deazahypoxanthine, the nucleosidic linkage is constructed by treatment of the epoxide of formula II with the metal salt (such as lithium, sodium, or potassium) of an appropriately substituted 1H-pyrrolo[2,3-d]pyrimidine, such as an appropriately substituted 4-halo-1H-pyrrolo[2,3-d]pyrimidine or optionally protected 4-amino-1H-pyrrolo[2,3-d]pyrimidine, which can be generated in situ by treatment with an alkali hydride (such as sodium hydride), an alkali hydroxide (such as potassium hydroxide), an alkali alkoxide (such as potassium t-butoxide), an alkali carbonate or bicarbonate (such as potassium carbonate and sodium bicarbonate), or an alkali amide base (such as sodium hexamethyldisilazane and lithium diisopropylamide) in a suitable anhydrous organic solvent, such as acetonitrile, diethyl ether, tetrahydrofuran, 1-methyl-2-pyrrolidinone, N,N-dimethylformamide (DMF), N,N-dimethylacetamide (DMAC), and mixtures thereof. The displacement reaction can be catalyzed by using a phase-transfer catalyst, such as TDA-1 or triethylbenzylammonium chloride, in a two-phase system (solid-liquid or liquid-liquid). The protecting groups in the protected nucleoside of structural formula IV are then cleaved following established deprotection methodologies, such as those described in T. W. Greene and P. G. M. Wuts, "Protective Groups in Organic Synthesis," $3^{rd}$ ed., John Wiley & Sons, 1999. Introduction of a primary amino group at the 4-position of the pyrrolo[2,3-d]pyrimidine nucleus can be effected by treatment of the 4-halo intermediate with alcoholic ammonia or liquid ammonia. These conditions will also cleave ester protecting groups at the 3- and 5-positions of the sugar residue. A 7H-pyrrolo[2,3-d]pyrimidin-4(3H)one (7-deazaguanine) compound may be derived by hydrolysis of the 4-halo intermediate with aqueous base, such as aqueous sodium hydroxide. Again these conditions will cleave ester protecting groups at the 3- and 5-positions of the sugar residue. If an optionally protected 4-amino-1H-pyrrolo[2,3-d]pyrimidine is used in the nucleophilic displacement reaction to generate the nucleosidic bond, the amine protecting group is then cleaved before, after, or simultaneously with cleavage of the protecting groups on the sugar residue. Illustratively, when PG represents an ester protecting group and the 4-amino group on the nucleobase is protected as its N-phthalimide derivative, all three protecting groups may be cleaved simultaneously by treatment with ammonia or an alkylamine, such as n-butylamine, neat or in the presence of an alcoholic solvent, such as methanol and ethanol.

In addition to protection as an N-phthalimide derivative, any nucleobase amino group may be protected as its amide (such as optionally substituted N-acetyl and N-benzoyl), carbamate (such as t-butyl, benzyl, 9-fluorenylmethyl, and allyl carbamate), and imine derivative [such as N-(N',N'-dimethylaminomethylene)amine, N-(methoxymethylene)amine, and optionally substituted N-benzylideneamine].

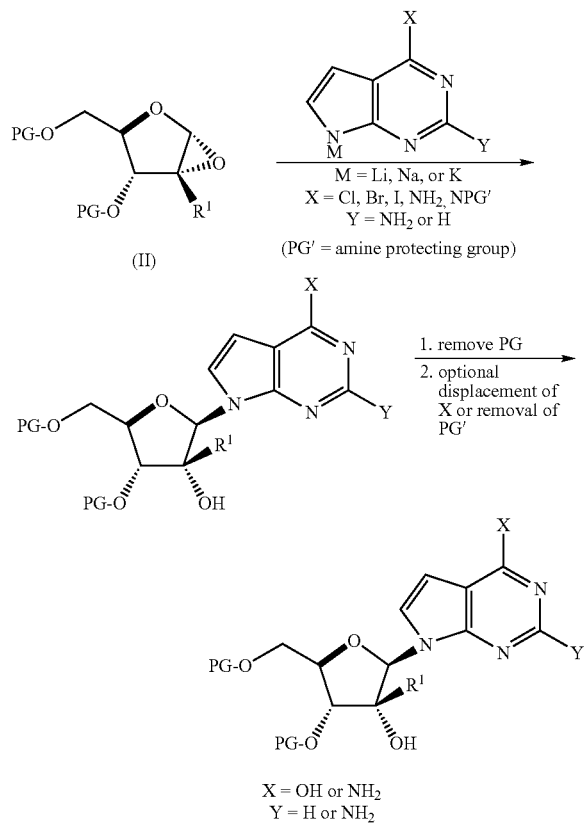

When B represents the pyrimidine nucleobase uracil or thymine, their bis-O-trimethylsilylated derivatives may be employed as nucleophiles in the reaction with the epoxide of structural formula II. The silylated derivatives of the nucleobase may be generated in situ with N,O-bis(trimethylsilyl)acetamide to effect silyl transfer to the nucleobase. When B represents cytosine, the N,O-bis(trimethylsilyl) derivative of $N^4$-acetyl or $N^4$-benzoyl-cytosine may be used as the nucleophile. The coupling reaction is carried out under the persilylation conditions of Vorbrüggen described in *Chem. Ber.*, 114: 1279 (1981) optionally in the presence of a Lewis acid, such as tin tetrachloride, zinc chloride, and trimethylsilyl trifluoromethanesulfonate (TMSOTf), in an organic solvent such as acetonitrile, tetrahydrofuran, diethyl ether, and methylene chloride. The cytosine amine protecting group (acetyl or benzoyl) is then cleaved by treatment of the derived nucleoside with methanolic ammonia, which conditions will also cleave any ester protecting group on the sugar hydroxyls.

When B represents adenine, silylated $N^6$-acetyl or $N^6$-benzoyladenine may be used as the nucleophile and the coupling reaction is carried out using the persilylation conditions of Vorbrüggen above. The adenine amine protecting group (acetyl or benzoyl) is then cleaved by treatment of the derived nucleoside with methanolic ammonia, which conditions will also cleave any ester protecting group on the sugar hydroxyls.

When B represents guanine, silylated 2-(acetylamino)-9H-purin-6-yl diphenylcarbamate may be used as the nucleophile and the coupling reaction is carried out using the persilylation conditions of Vorbrüggen above. The guanine amine and hydroxyl protecting groups (acetyl and diphenylaminocarbonyl, respectively) are then cleaved by treatment of the derived nucleoside with methanolic ammonia or hydrazine hydrate, which conditions will also cleave any ester protecting group on the sugar hydroxyls.

Representative experimental procedures utilizing the novel process of the present invention are detailed below. The following Examples are provided for purposes of illustration only and are not intended to limit the process of the present invention to the specific conditions for making the compound.

By halogen is meant fluorine, chlorine, bromine, or iodine. By "Phth" is meant phthaloyl.

The "squiggly" bond at the anomeric position of the furanose ring in the intermediate of structural formula III is intended to signify undefined stereochemistry at this stereogenic center. Thus, the process of the present invention is intended to encompass the individual α- and β-anomers of the intermediate of structural formula III as well as all mixtures thereof as starting materials for the instant process.

All X-ray patterns were obtained on a Philips 3100 diffractometer, using Cu Kα radiation, from 2° to 40° (2θ), using a collection time of 8 min. All DSC thermograms were taken on a TA 2920 Differential Scanning Calorimeter with a heating rate of 10° C./minute under a nitrogen atmosphere. The carbon-13 CPMAS nuclear magnetic resonance (NMR) spectra were obtained on a Bruker DSX 400WB NMR system using a Bruker 4 mm double resonance CPMAS probe while spinning the sample at 15.0 kHz. The NMR experiments involved $^1H/^{13}C$ cross-polarization magic-angle spinning with variable-amplitude cross-polarization. A total of 512 scans were collected for the spectra with a contact time of 2.0 msec and recycle delay of 5 s. The $^{13}C$ spectrum is referenced to TMS using the carbonyl carbon of glycine (176.03 ppm) as a secondary reference. The thermogravimetric analysis (TGA) was performed on a Perkin-Elmer TGA-7 Thermal Analysis series at a heating rate of 10° C./min with a nitrogen purge.

EXAMPLE 1

4-Amino-7-(2-C-methyl-β-D-ribofuranosyl)-7H-pyrrolo[2,3-d]pyrimidine (2'-C-methyl-7-deazaadenosine) (4-3)

Preparation of Intermediates:

1. 2-C-Methyl-3,5-di-O-(p-toluoyl)-D-ribofuranose (2-2)

Scheme 2

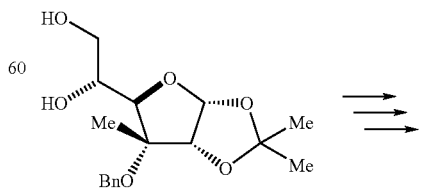

2-1

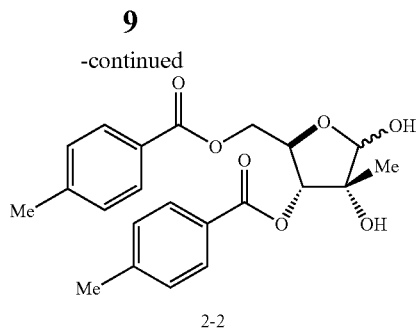

To a solution of 3-O-benzyl-1,2-O-isopropylidene-3-C-methyl-α-D-allofuranose (2-1) (for preparation, see *Carbohydr. Res.*, 44: 275-283 (1975) (5.0 kg, 15.4 mol) and pyridine (3.7 kg, 46.2 mol) in 35 L of acetonitrile was added p-toluoyl chloride (5.2 kg, 33.9 mol), and the reaction was heated at 50-55° C. for 12 h. A solution of 6.0 L (46.2 mol) of 48 wt % HBF$_4$ (tetrafluoroboric acid) in 9 L of water was added at 50-55° C. After 2 h, 10 L of acetonitrile was distilled off, and 10 L acetonitrile was added. At 97% conversion, 10 L of acetonitrile was distilled off, and the reaction solution was cooled to 0-5° C. A solution of periodic acid (4.2 kg, 18.5 mol) in 10 L of water was added. After the reaction was aged for 30 min, 35 L of isopropyl acetate and 10 L of water were added. The organic phase was washed with 25 L of water followed by 20 L of aqueous NaHCO$_3$, 15 L of 5% sodium thiosulfate in water, and 15 L of water. The isopropyl acetate solution was concentrated to 10-15 L, and 40 L of methanol was added. The solution was cooled to 0° C. and diisopropylamine (0.78 kg, 7.7 mol) was added. After 2 d at 0° C., aqueous HCl (1N, 7.7 L) was added at 0-5° C. followed by 30 L of isopro acetate and 40 L of water. The organic phase was washed with aqueous 1N HCl, NaHCO$_3$, and brine. The organic phase was dried through azeotropic distillation and treated with activated carbon. The carbon was removed by filtration and the resulting solution was diluted to 75 L with isopropyl acetate and hydrogenated (45 psi, 50° C., 1.5 kg 10% Pd/C) for 24 h. The filtrate was concentrated to 15 L and 60 L of heptane was added at 50° C. The crystalline product was isolated by filtration washing with a 10 L of 20% isopropyl acetate in heptane. Drying afforded 4.03 kg of the desired diol 2-2.

$^1$H NMR (CDCl$_3$, 400 MHz): The ratio of α:β isomers in CDCl$_3$ is about 5 to 1. For the major isomer: δ 7.95-7.90 (m, 4H), 7.26 (d, J=8.0 Hz, 2H), 7.17 (d, J=8.0 Hz, 2H), 5.53 (d, J=7.2 Hz, 1H), 5.22 (d, J=2.8 Hz, 1H), 4.65-4.49 (m, 3H), 3.08 (d, J=3.2 Hz, 1H), 2.44 (s, 3H), 2.38 (s, 3H), 2.26 (s, 1H), 1.44 (s, 3H) ppm; for the minor isomer: δ 7.95-7.90 (m, 4H), 7.27 (d, J=8.0 Hz, 2H), 7.22 (d, J=8.0 Hz, 2H), 5.16 (d, J=5.6 Hz, 1H), 5.12 (d, J=5.6 Hz, 1H), 4.66-4.49 (m, 3H), 3.54 (d, J=5.6 Hz, 1H), 2.91 (s, 1H), 2.43 (s, 3H), 2.40 (s, 3H), 1.44 (s, 3H) ppm. $^{13}$C NMR (CDCl$_3$, 100 MHz): δ 166.6, 166.3, 165.9, 165.7, 144.6, 144.3, 143.8, 143.7, 129.9, 129.7, 129.3, 129.2, 129.1, 129.0, 127.0, 126.9, 126.4, 126.2, 102.9, 100.8, 79.8, 79.2, 78.7, 76.9, 76.5, 76.4, 65.5, 64.0, 23.5, 21.7, 21.6, and 20.0 ppm.

2. 4-Phthalimido-7H-pyrrolo[2,3-d]pyrimidine (3-2)

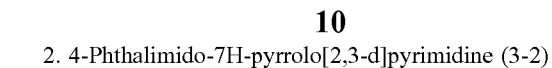

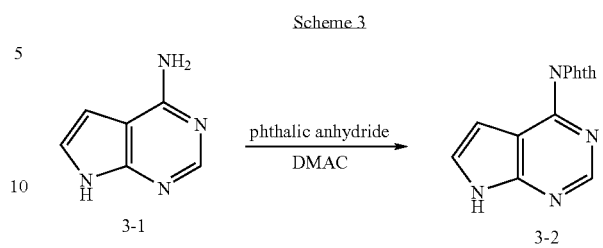

To a 250 mL three-neck round bottom flask equipped with an overhead stirrer, nitrogen inlet, and thermocouple was charged 50 mL of dry N,N-dimethylacetamide followed by 5.0 g of 7H-pyrrolo[2,3-d]pyrimidin-4-ylamine (3-1) [J. Davoll, *J. Chem. Soc.*, 131-138 (1960)] and 11.6 g of phthalic anhydride. The resulting mixture was heated to 80° C. for 8 h and then cooled to 10° C. Water (40 mL) was added while maintaining the temperature below 15° C. The resulting slurry was aged for 4 h, then filtered, and the filter washed with 20 mL of 1:1 (v/v) dimethylacetamide/water followed by 30 mL of water. The cake was sucked dry, then washed with 50 mL of ethyl acetate. The solid was dried at 40° C. under vacuum with a nitrogen sweep to give 8.1 g of 4-phthalimido-7H-pyrrolo[2,3-d]pyrimidine (3-2); m.p. 276-277° C.

$^1$H NMR (DMSO-d$_6$, 400 MHz): δ 12.14 (s, 1H), 8.79 (s, 1H), 8.01 (dd, J=5.5, 3.1 Hz, 2H), 7.92 (dd, J=5.5, 3.1 Hz, 2H), 7.63 (dd, J=3.5, 2.4 Hz, 1H), 6.56 (dd, J=3.5, 1.8 Hz, 1H); $^{13}$C NMR (DMSO-d$_6$, 100 MHz): δ 166.3, 154.2, 151.0, 145.2, 135.7, 132.0, 128.7, 124.4, 115.2, 100.1.

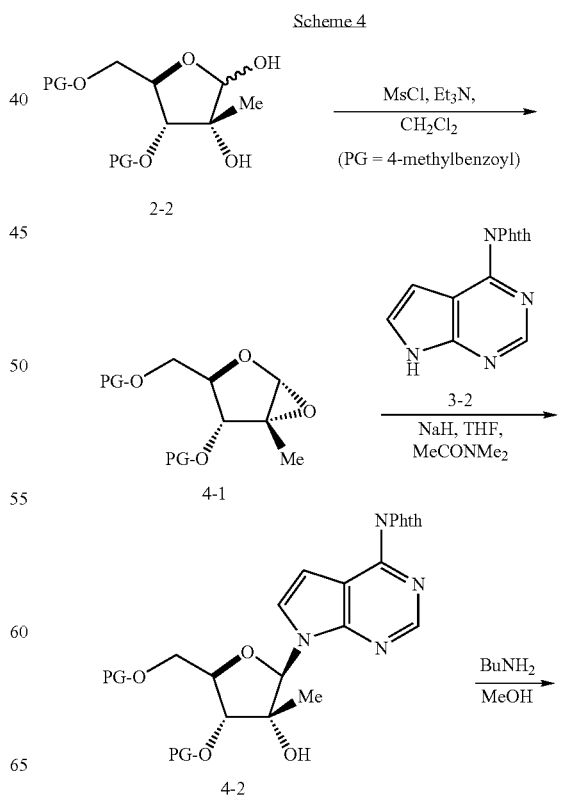

-continued

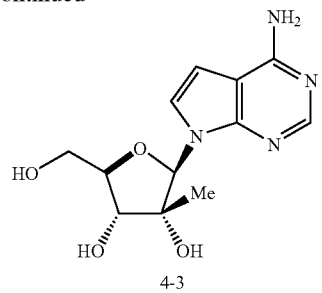

4-3

Step A: 1,2-Anhydro-3,5-di-O-(p-toluoyl)-2-C-methyl-α-D-ribofuranose (4-1)

To a 72 L vessel was charged dry dichloromethane (32 L), triethylamine (3.0 L), and diol 2-2 (3.44 kg, 90 wt % pure). The mixture was warmed to 30° C., then methanesulfonyl chloride (0.79 L) was added over 40 min. After 1 h, the batch was partitioned between pH 7 buffer (20 L) and methyl tert-butyl ether (44 L). The organic phase was washed with 1M aqueous NaCl (38 L) then switched to toluene by vacuum distillation followed by concentration to about 9 L. The resulting solution of epoxide was used directly in Step B.

Step B: 4-Phthalimido-7-[3,5-di-O-(p-toluoyl)-2-C-methyl-β-D-ribofuranosyl]-7H-pyrrolo[2,3-d]pyrimidine (4-2)

Tetrahydrofuran (5.4 L), sodium hydride (146 g of 60% dispersion in oil, unwashed), and N,N-dimethylacetamide (4 L) were charged to a 72 L flask and the suspension was cooled to 0° C. 4-Phthalimido-7H-pyrrolo[2,3-d]pyrimidine (3-2) (2.08 kg) was added to the reaction while maintaining the temperature below 25° C. N,N-Dimethylacetamide (1.4 L) was added followed by the solution of the epoxide (2.75 assay kg) in toluene from Step A, and the reaction mixture was heated at 50-90° C. for 9 h. After cooling to ambient temperature, ethyl acetate (19 L) and aqueous $KH_2PO_4$ (0.97 kg in 19 L of water) were added. The organic phase was washed with water. The resulting organic solution was solvent-switched to toluene by vacuum distillation (T<40° C.) to give a final volume of 10 L.

Step C: 4-Amino-7-(2-C-methyl-β-D-ribofuranosyl)-7H-pyrrolo[2,3-d]pyrimidine (4-3)

To the toluene solution from Step B at ambient temperature were added methanol (25 L) and n-butylamine (3.13 kg, 42.9 mol). The reaction mixture was aged at 64° C. for 24 to 30 h. The mixture was concentrated to about 9 L, and 9 L of methanol was added. The solution was concentrated to 9 L, and the resulting slurry was aged at 60° C. for 60 min. Toluene (13 L) was added over 1.5 h. The slurry was aged at 60° C. for another 2 h and then allowed to cool to ambient temperature. The solid was filtered and the wet cake was washed with 9 L of 20% methanol in toluene then 9 L of 10% methanol in toluene. The solid was suction dried at ambient temperature under nitrogen to give 1.79 kg (94 wt % pure) of the title nucleoside 4-3 as the toluene solvate.

The X-ray powder diffraction pattern of the crystalline toluene solvate displayed characteristic diffraction peaks corresponding to d-spacings of 16.93, 12.16, 6.04, 5.95, 5.71, 4.62, 3.34, and 3.12 angstroms.

The crystalline toluene solvate was also characterized by solid-state NMR spectroscopy. The carbon-13 CPMAS NMR spectrum exhibited signals with chemical shift values at 156.1, 150.0, 127.3, 124.3, 122.3, 121.1, 104.3, 99.6, 97.6, 90.9, 82.6, 80.6, 73.3, 72.4, 71.0, 64.9, 64.0, 60.9, 20.3, and 17.9 ppm.

The differential scanning calorimeter (DSC) curve for the crystalline toluene solvate exhibited a melting endotherm with a low temperature shoulder at approximately 200° C. Integration of this endotherm using a sigmoidal baseline fitting gave an onset temperature of 221.0° C., a peak temperature of 223.9° C., and an associated heat of 143 Joules/g.

Thermogravimetric analysis (TGA) indicated a weight loss of about 3.0% from ambient temperature to about 233° C.

Final Recrystallization or Hot Swish in 1-Propanol:

A) The nucleoside 4-3 (30 assay g) was dissolved in 240 mL of 25% water in 1-propanol at 50° C. and the resulting solution was seeded. The water concentration was reduced to 2% by azeotropic distillation at reduced pressure while maintaining the volume constant with the addition of 1-propanol. The slurry was cooled to about 20° C. and the crystallized product was isolated by filtration to give 28.1 g of the unsolvated anhydrous crystalline form after suction drying at ambient temperature.

B) The nucleoside 4-3 (3.01 assay kg) was dissolved in 24 L of 2% water in 1-propanol and the slurry was heated at 60-65° C. for 4 h. After cooling to about 20° C., the crystalline solid was isolated by filtration to give 2.79 kg of the nucleoside as the unsolvated anhydrous crystalline form.

The X-ray powder diffraction pattern of the crystalline anhydrate displayed characteristic diffraction peaks corresponding to d-spacings of 8.14, 6.11, 6.00, 5.96, 4.62, 4.06, 3.74, and 3.34 angstroms.

The crystalline anhydrate was also characterized by solid-state NMR spectroscopy. The carbon-13 CPMAS NMR spectrum exhibited signals with chemical shift values at 157.7, 149.3, 147.0, 119.1, 102.8, 102.2, 90.7, 81.5, 79.3, 77.7, 66.5, and 19.9 ppm.

The differential scanning calorimeter DSC) curve for the crystalline anhydrate exhibited a melting endotherm with a peak temperature of 223.9° C., an onset temperature of 222.2° C., and an associated heat of 182 Joules/g.

Thermogravimetric analysis (TGA) indicated a weight loss of about 0.2% from about 149° C. to about 237° C.

High-performance Liquid Chromatography (HPLC) Assay Conditions:

| Column: | Aquasil C18, 100 × 4.6 mm, 5 micron particle size | | |
|---|---|---|---|
| Gradient: | Time (min) | MeCN | 10 mM phosphate, pH 6.5 |
| | 0 | 5% | 95% |
| | 20 | 70% | 30% |
| | 26 | 70% | 30% |
| Flow rate: | 1 mL/min | | |
| Detection: | 220 nm | | |
| Retention time for compound 4-3: | 8.2 min | | |

What is claimed is:

1. A process for preparing a compound of structural formula I:

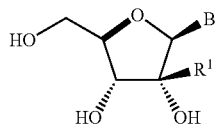

wherein $R^1$ is $C_{1-6}$ alkyl and B is a purine or pyrimidine nucleobase selected from the group consisting of cytosine, uracil, thymine, hypoxanthine, adenine, guanine, 7-deazaguanine, 7-deazaadenine, 7-deaza-2,6-diaminopurine, and 7-deazahypoxanthine;
comprising the steps of
(a) producing a compound of structural formula IV:

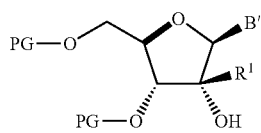

wherein B' is optionally protected B,
by contacting a compound of structural formula II:

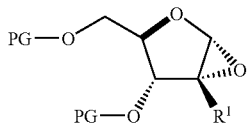

wherein PG is a hydroxyl protecting group,
with a nucleophile B' in a suitable organic solvent; and
(b) removing the hydroxyl protecting groups PG and optional protecting groups in B'.

2. The process of claim 1 additionally comprising the step of producing a compound of structural formula II:

(II)

by treating a compound of structural formula III:

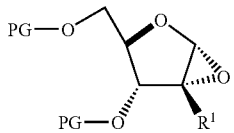

with a sulfonylating or halogenating agent in a suitable organic solvent in the presence of base, wherein said base is added before, during, or after said treatment with said sulfonylating or halogenating agent.

3. The process of claim 1 wherein B is guanine, cytosine, adenine, or 7-deazaadenine.

4. The process of claim 3 wherein B is 7-deazaadenine.

5. The process of claim 1 wherein $R^1$ is methyl.

6. The process of claim 4 wherein $R^1$ is methyl.

7. The process of claim 1 wherein said hydroxyl protecting group is an ester, silyl ether, or optionally substituted benzyl ether protecting group.

8. The process of claim 7 wherein said hydroxyl protecting group is an ester protecting group.

9. The process of claim 8 wherein said ester protecting group is a benzoate ester unsubstituted or substituted with one to two groups independently selected from halogen, cyano, methoxy, nitro, and methyl.

10. The process of claim 2 wherein the compound of structural formula II is produced by treating a compound of structural formula III with a sulfonylating agent in a suitable organic solvent in the presence of base.

11. The process of claim 10 wherein said sulfonylating agent is methanesulfonyl chloride.

12. The process of claim 10 wherein said base is an amine base selected from the group consisting of triethylamine, pyridine, 4-(dimethylamino)pyridine, N,N-diisopropylethylamine, and diisopropylamine.

13. A process for preparing a compound of structural formula I:

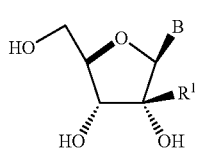

wherein $R^1$ is $C_{1-6}$ alkyl and B is a purine or pyrimidine nucleobase selected from the group consisting of cytosine, uracil, thymine, hypoxanthine, adenine, guanine, 7-deazaguanine, 7-deazaadenine, 7-deaza-2,6-diaminopurine, and 7-deazahypoxanthine;
comprising the steps of:
(a) producing a compound of structural formula (II)

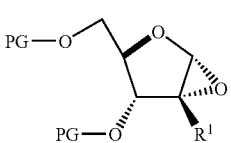

wherein PG is a hydroxyl protecting group,
by treating a compound of structural formula III:

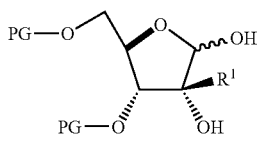

with a sulfonylating or halogenating agent in a suitable organic solvent in the presence of base, wherein said base is added before, during, or after treatment with said sulfonylating or halogenating agent;

(b) producing a compound of structural formula IV:

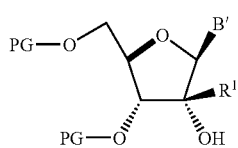
(IV)

wherein B' is optionally protected B, by contacting a compound of structural formula II:

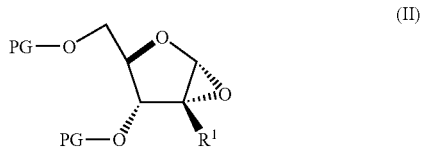
(II)

with a nucleophile B' in a suitable organic solvent; and (c) removing the hydroxyl protecting groups PG and optional protecting groups in B'.

* * * * *